US005813614A

United States Patent [19]

Coffee

[11] Patent Number: 5,813,614
[45] Date of Patent: Sep. 29, 1998

[54] DISPENSING DEVICE

[75] Inventor: Ronald Alan Coffee, Haslemere, United Kingdom

[73] Assignee: Electrosols, Ltd., Surrey, United Kingdom

[21] Appl. No.: 718,563

[22] PCT Filed: Mar. 28, 1995

[86] PCT No.: PCT/EP95/01162

§ 371 Date: Sep. 30, 1996

§ 102(e) Date: Sep. 30, 1996

[87] PCT Pub. No.: WO95/26235

PCT Pub. Date: Oct. 5, 1995

[30] Foreign Application Priority Data

Mar. 29, 1994 [GB] United Kingdom .................. 9406255

[51] Int. Cl.[6] .................................................. B05B 5/00

[52] U.S. Cl. ......................... 239/690; 239/692; 239/704

[58] Field of Search ............................... 239/690, 690.1, 239/692, 704, 708

[56] References Cited

U.S. PATENT DOCUMENTS

| | | | |
|---|---|---|---|
| 3,096,762 | 7/1963 | Winchell | 128/190 |
| 3,232,292 | 2/1966 | Schaefer | 128/172 |
| 3,456,646 | 7/1969 | Phillips et al. | 128/173 |
| 3,837,573 | 9/1974 | Wagner | 239/15 |
| 3,897,905 | 8/1975 | Tadewald | 239/15 |
| 3,930,061 | 12/1975 | Scharfenberger | 427/27 |
| 3,958,959 | 5/1976 | Cohen et al. | 55/10 |
| 4,073,002 | 2/1978 | Sickles et al. | 361/227 |

(List continued on next page.)

FOREIGN PATENT DOCUMENTS

| | | |
|---|---|---|
| 0029301A1 | 5/1981 | European Pat. Off. . |
| 0 120 633 A2 | 10/1984 | European Pat. Off. . |
| 0 102 713 B1 | 9/1987 | European Pat. Off. . |
| 0234842 | 9/1987 | European Pat. Off. . |
| 0 243 031 A1 | 10/1987 | European Pat. Off. . |
| 0250164A3 | 12/1987 | European Pat. Off. . |
| 0523963A1 | 7/1992 | European Pat. Off. . |
| 0523962A1 | 1/1993 | European Pat. Off. . |
| 523964A1 | 1/1993 | European Pat. Off. . |
| P 2008769 | 9/1970 | Germany . |
| 4106564A1 | 9/1992 | Germany . |
| 191545 | 11/1983 | New Zealand . |
| 195704 | 9/1984 | New Zealand . |
| 198774 | 12/1984 | New Zealand . |
| 1005939A | 6/1981 | U.S.S.R. . |
| 1297993 | 11/1972 | United Kingdom . |
| 2018627 | 10/1979 | United Kingdom . |
| 2018627B | 10/1979 | United Kingdom . |
| 1569707 | 6/1980 | United Kingdom . |
| 2 128 900 A | 5/1984 | United Kingdom . |
| 2 201 873 A | 9/1988 | United Kingdom . |
| WO 91/07232 | 5/1991 | WIPO . |
| WO 92/15339 | 9/1992 | WIPO . |
| W0 93/06937 | 4/1993 | WIPO . |

OTHER PUBLICATIONS

Article entitled: *Electro–osmosis Controls Fluid in Novel Transducer Concept by Product Engineering*, dated Jul. 4, 1970 authored by: Ray Lewis, Cleveland; pp. 71–72.

Article entitled: *Electrodynamic Crop Spraying*, dated 1981; authored by; R. A. Coffee; Reprinted from Outlook on Agriculture vol. 10, No. 7, 1981; includes excerpt pp. 350–356.

*Primary Examiner*—Andres Kashnikow
*Assistant Examiner*—Robin O. Evans
*Attorney, Agent, or Firm*—Cobrin Gittes & Samuel

[57] ABSTRACT

A device for dispensing a liquid for inhalation, which comprises an unshielded electrohydrodynamic comminution means (1), a means for supplying a liquid to the comminution means, a sharp discharge electrode (12) and, optionally, a means for charging the discharge electrode to a polarity opposite to that of the comminution means, wherein the discharge electrode is located so as to direct gaseous ions into the body of the comminuted liquid and thereby to fully or partially discharge the comminuted liquid.

15 Claims, 3 Drawing Sheets

U.S. PATENT DOCUMENTS

| | | | |
|---|---|---|---|
| 4,150,644 | 4/1979 | Masaki et al. | 123/119 |
| 4,186,886 | 2/1980 | Sickles | 239/691 |
| 4,203,398 | 5/1980 | Maruoka | 123/119 |
| 4,266,721 | 5/1981 | Sickles | 239/3 |
| 4,356,528 | 10/1982 | Coffee | 361/226 |
| 4,439,980 | 4/1984 | Biblarz et al. | 60/39.06 |
| 4,467,961 | 8/1984 | Coffee et al. | 239/1 |
| 4,476,515 | 10/1984 | Coffee | 361/226 |
| 4,508,265 | 4/1985 | Jido | 239/3 |
| 4,509,694 | 4/1985 | Inculet et al. | 239/697 |
| 4,549,243 | 10/1985 | Owen et al. | 361/228 |
| 4,659,012 | 4/1987 | Coffee | 239/3 |
| 4,671,269 | 6/1987 | Wilp | 128/202.25 |
| 4,735,364 | 4/1988 | Marchant | 239/690.1 |
| 4,748,043 | 5/1988 | Seaver et al. | 427/30 |
| 4,749,125 | 6/1988 | Escallon et al. | 239/3 |
| 4,776,515 | 10/1988 | Michalchik | 239/3 |
| 4,788,016 | 11/1988 | Colclough et al. | 264/10 |
| 4,801,086 | 1/1989 | Noakes | 239/3 |
| 4,846,407 | 7/1989 | Coffee et al. | 239/690 |
| 4,962,885 | 10/1990 | Coffee | 239/3 |
| 4,979,680 | 12/1990 | Bauch et al. | 239/692 |
| 5,044,564 | 9/1991 | Sickles | 239/690.1 |
| 5,086,972 | 2/1992 | Chang et al. | 239/3 |
| 5,222,663 | 6/1993 | Noakes et al. | 239/3 |
| 5,267,555 | 12/1993 | Pajalich | 128/200.14 |
| 5,381,789 | 1/1995 | Marquardt | 128/202.25 |
| 5,409,162 | 4/1995 | Sickles | 239/3 |
| 5,483,953 | 1/1996 | Cooper | 128/200.22 |

DISPENSING DEVICE

The invention relates to a dispensing device for comminuting a liquid and the use of such a device, in particular, in medicine.

Dispensing devices are known which produce a finely divided spray of droplets generated by applying an electric field to a liquid at a spray head or spray edge. The strength of the electric field is sufficiently high to comminute liquid issuing from the spray head. The droplets produced are electrically charged and thus are prevented from coagulating by mutual repulsion. This is known as electrohydrodynamic comminution.

United Kingdom patent number 1569707 describes an electrohydrodynamic spray device principally for use in crop spraying. An essential component of the GB 1569707 spray device is a field intensifying electrode, cited adjacent the spray head. The field intensifying electrode is stated to reduce the incidence of corona discharge and allows lower electric field strengths to be used during spray generation.

U.S. Pat. No. 4801086 discloses an electrohydrodynamic spray device which produces multiple spray streams.

United Kingdom patent number 2018627B discloses an electrohydrodynamic spray device wherein the droplet spray is fully or partially discharged by means of an earthed electrode having a sharp or pointed edge and located downstream of the spray head. The GB 2018627B spray device does not comprise the field intensifying electrode of GB 1569707.

European Patent number 0234842 discloses an inhaler which uses electrohydrodynamic spray technology. In use, the spray of charged droplets is discharged prior to inhalation by means of a sharp discharge electrode carrying an opposite charge to the droplet spray and located downstream of the spray head. The droplets are discharged to facilitate droplet deposition into the respiratory tract by preventing deposition of charged droplets onto the mouth and throat of the user. The EP 0234842 spray device does not comprise the field intensifying electrode of GB 1569707.

An essential requirement of the EP 0234842 electrohydrodynamic inhaler is a neutral shield electrode which is stated to be required to prevent the corona from the sharp discharge electrode from adversely affecting the formation of the spray. It has now surprisingly been discovered that a shield electrode is not required for effective spray discharge or partial discharge.

According to the present invention, there is provided a dispensing device, comprising an exposed, unshielded comminution site, means for supplying liquid to the comminution site, means for charging the comminution site to a potential for causing electrohydrodynamic comminution of liquid supplied to the comminution site, a discharge electrode for at least partially discharging comminuted matter, means for charging the discharge electrode to a polarity opposite to that of the comminution site to cause ionization of gaseous molecules in the vicinity of the discharge electrode, the discharge electrode being arranged so as to face towards the comminution site to cause gaseous ions produced by the discharge electrode to be directed towards the comminution site to at least partially discharge comminuted matter produced by the comminution site.

In an embodiment, the present invention provides a dispensing device comprising a field guard electrode located so as to regulate the amount of discharge by the discharge electrode. In one example, the field guard electrode, which may be an annular electrode, is arranged to effect such regulation by adjustably altering the effective shape of the discharge electrode, for example by adjustably enclosing or surrounding the discharge electrode, for example by a screw thread adjustment means.

The device may be adapted to be portable.

A device embodying the invention may be adapted into any form which dispenses comminuted matter for inhalation, for medicinal and non-medicinal use. A suitable non-medicinal use includes the dispensing of a perfume or an aroma. A suitable non-medicinal use includes the dispensing of a biocide or an insecticide.

Preferably, the device is in the form of an inhaler, for the inhaled delivery of a medicament and a preferred liquid is a liquid medicament formulation adapted for inhaled administration.

Medicaments suitable for adaption for inhaled administration include those used for the treatment of disorders of the respiratory tract, such as reversible airways obstruction and asthma and those used in the treatment and/or prophylaxis of disorders associated with pulmonary hypertension and of disorders associated with right heart failure by inhaled delivery.

The electrohydrodynamic comminution means may be any conventional electrohydrodynamic comminution means, for example those described in the above mentioned patent specifications.

Suitable liquid formulations include medicament formulations, perfume or aroma formulations.

Suitably, the comminution means comprises a comminution surface or edge and means for electrically charging the liquid at the said surface or edge to a potential sufficient to provide comminution of the liquid, the potential usually being of the order of 1–20 kilovolts.

One comminution surface or edge is provided by the end surface of a bundle of fibres, the fibres being so aligned that liquid flows along the length of the fibres and between the interstitial spaces defined by the fibres to the said end surface.

Suitable fibres are fibres of ceramic, such as glass, or polymer such as polyester or nylon.

A preferred comminution surface or edge is provided by a thin capillary tube or a slot defined by two parallel plates or concentric tubes.

The means for supplying a liquid to the comminution means may be any appropriate mechanical or electrical liquid supplying means such as a syringe pump or an electrically powered pump as described in EP 0029301. In an embodiment, the present invention provides a dispensing device which, in use, may provide liquid droplets within the range of from 0.1 to 500 microns in diameter, more usually from 1.0 to 200 microns and preferably, for topical application, diameters in the range of from 5.0 to 100 microns.

The comminution means of the dispenser provides liquid droplets within the range of from 0.1 to 500 microns in diameter, more usually from 1.0 to 200 microns and preferably, for topical application, diameters in the range of from 5.0 to 100 microns.

For a given liquid the diameter of the droplets can be controlled by varying the applied voltage and liquid flow rate using routine experimental procedures. However, liquids having viscosities within the range of from 1 to 500 centipoise and resistivities in the range of from $10^2$–$10^8$ ohm m can be comminuted by the present device.

In an embodiment, the present invention provides a dispensing device which, in use, may provide electrically charged droplets of accurately controlled sizes which may then be used to deliver drugs to the pulmonary membranes by inhalation, or to the blood stream by inhalation to the terminal airways. Currently available aerosol generators commonly used for medical purposes, such as, for example, asthma aerosol droplet or powder delivery units have generally a polydisperse nature. That is to say that the droplet or particle size range produced by ordinary aerosol generators will contain sizes above and below those believed to be optimally beneficial in any medical drug delivery operation. For example, asthma dispensers often have more than ninety percent of the volume of drug delivered at diameters greater than 10.0 µm. It is believed that the droplets or particles of such diameters will not enter the middle airways of the lung, where they are required, and will thus be imbibed by the patient through the upper airways, with little or no therapeutic result, and with possible side effects. Also, droplets or particles of less than about 1.00 µm may be present and may flow through to the terminal airways, where they could be rapidly systemically imbibed, thus also risking side effects, without therapeutic benefit.

The ideal droplet dispenser for delivery of medicament to the lower respiratory tract would be able to produce droplets in very narrow (monodisperse) size spectra, say all below 10.0 µm. It would be better still if all droplets could be made to be within a range of +/−25 percent or better, with average size controllable anywhere in the range of 0.1 µm to 10.00 µm, especially 3 µm to 10.00 µm for inhalation therapy. Further benefits would accrue if the same device could process reactive fluid mixtures by use of electric field turbulence at the instant of spraying droplets, so that no reaction could take place before application.

As described above electrohydrodynamic spray devices are known which produce multiple spray streams. However such devices are not known to be applied to the administration of liquid formulations for inhalation. Accordingly, in an embodiment the present invention provides a dispensing device for liquid. formulations for inhalation which comprises a mixing nozzle as described in U.S. Pat. No. 4801086.

Thus, by inducing electric field turbulence, two or more liquid components can be mixed at the moment of delivery. This is an essential requirement for ingredients which would react too early if premixed. By reacting too soon before application, they may lose their intended properties or, for example the mixture may increase its viscosity so as to become unsprayable. Such an instantaneous mixing facility at the point and time of application of the mixture has not previously been possible.

The process of droplet production may require total, or partial discharge of droplets when used for inhalation. A zero charge ensures that droplets are deposited into the required respiratory area or areas, by mass differentiation, in accordance with the agreed opinion, as published in the medical literature (see "Inhalation Studies" edited by R. F. Phalen, published by CRC Press, 1984). Additionally, by retaining a specific, generally reduced charge, it may be possible to further increase the specificity of the zone of deposition within the respiratory system.

When used herein 'unshielded electrohydrodynamic comminution means' relates to a comminution means which does not have a neutral shield electrode as defined in EP 0234842.

When used herein 'medicament' includes proprietary medicines, pharmaceutical medicines and veterinary medicines.

When used herein, unless more specifically defined herein, 'inhaled administration' includes administration to and via the upper respiratory tract, including the nasal mucosa, and the lower respiratory tract.

The liquid medicinal formulations for use in the device of the invention may be formulated according to conventional procedures, such as those disclosed in the US Pharmacopoeia, the European Pharmacopoeia, 2nd Edition, Martindale The Extra Pharmacopoeia, 29th Edition, Pharmaceutical Press and the Veterinary Pharmacopoeia.

The liquid perfume or aroma formulations for use in the device of the invention may be formulated according to conventional procedures, such as those disclosed in Harry's Cosmeticology, 9th Edition, 1982, George Goodwin, London.

BRIEF DESCRIPTION OF THE DRAWINGS

Embodiments of the present invention will now be described, by way of example, with reference to the accompanying drawings, in which.

DESCRIPTION OF THE PREFERRED EMBODIMENT (1) Nozzles

Figure 1:
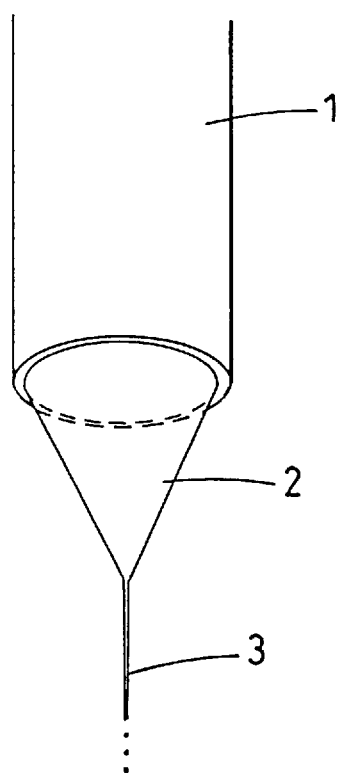
FIGS. 1 to 3 show various types of comminution site.
Figure 2:
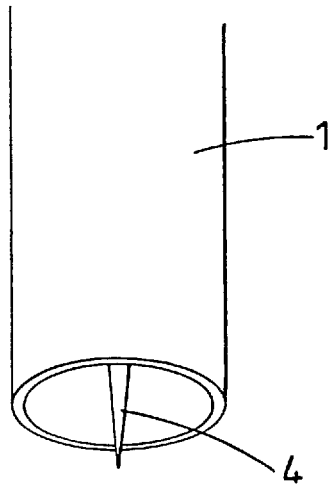
Figure 3:
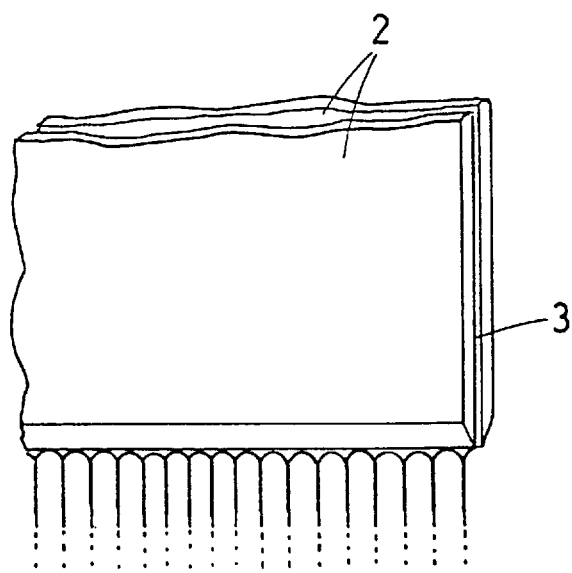

FIGS. 1 shows a thin-walled capillary tube (1), made of conducting, semiconducting or electrically insulating material and electrically connected to a source of high-voltage direct-current, either directly or through the liquid. A single jet (3) is produced from a cusp (2) of liquid, both of which form naturally, according to the voltage and flow rate for a given liquid. FIG. 2 shows a conducting, semiconducting or insulating cylinder (1) which may have a larger diameter than those shown in FIG. 1. This nozzle has an innermember (4) which is approximately coaxial with the outer tube, (1). FIG. 3 shows a slot nozzle, formed between two parallel plates (2) having conducting, semiconducting or insulating edges electrically connected to a high-voltage direct-current supply, from which the liquid emerges, forming cusps and jets when the voltage supply and liquid flow rates are suitably adjusted according to the type of liquid being sprayed. For a given jet (and thus droplet) size, and a given liquid, this nozzle may enable a higher flow rate to be achieved than those in which a single cusp and jet are used.

(2) Flow Inducers

Figure 4:
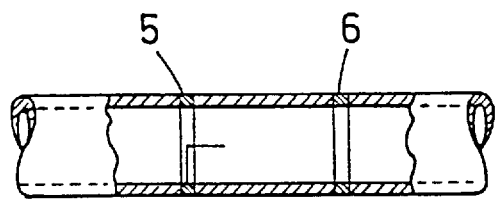
FIG. 4 shows one example of liquid supplying means.

An example of such a device is that illustrated in FIG. 4 which shows an ion stream flow inducer, wherein a high voltage electrode (5) breaks up pairs of charge carriers within the liquid, thus neutralizing those of opposite polarity at the electrode, and leaving a large population of monionized like-polarity charge carriers which stream away from the high voltage electrode by coulombic force, thus moving the liquid in the direction of the counter electrode (6) by means of viscous drag. This pumping means requires that an electrode (5) is able to effectively inject like-polarity charge carriers into the liquid, close to the electrode (5). This may be effectively done by using a sharp-edged conducting or semiconducting surface, held at a sufficiently high potential to disrupt lightly bonded charge carriers or to ionize the liquid. Normally, it is only possible to establish a strong enough field for both creating unipolar charge carriers and pumping the liquid, when the liquid is of sufficient resistivity. Typically a resistivity of, say 10 (exp. 8) ohm meters, will pump at several millilitre per minute, with a head of up to one meter, at a voltage of 10 to 20 kilovolts, and a direct current of only a few microamperes. More conductive liquids will draw more current and will establish a weaker electric field. Thus highly conducting liquids, such as, say tap water may not readily establish a practicable drag pressure.

(3) Reactive Liquid Mixing

Figure 5:
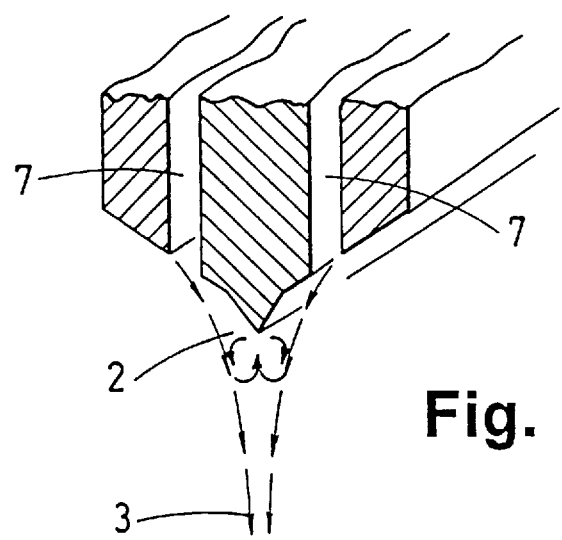
FIGS. 5 and 6 show examples of comminution sites or nozzles for mixing liquids.

Two or more liquids may be mixed after emerging from the nozzle by maximizing turbulent motion which can be induced within the cusp (2) which forms the base of each liquid jet (3). FIG. 5 shows a nozzle formed by three parallel plates, forming two slot-gaps (7) through which two liquids, a and b, are induced to flow, and to subsequently become mixed in the cone-shaped liquid base (2) of each jet, in accordance with eddy currents that can be induced as shown. This mixing may be maximized by using a liquid formulation having the lowest possible viscosity for each liquid; the maximum nozzle potential; and an optimal flow rate and degree of asymmetry of the individual flow rates of the component liquids.

Figure 6:
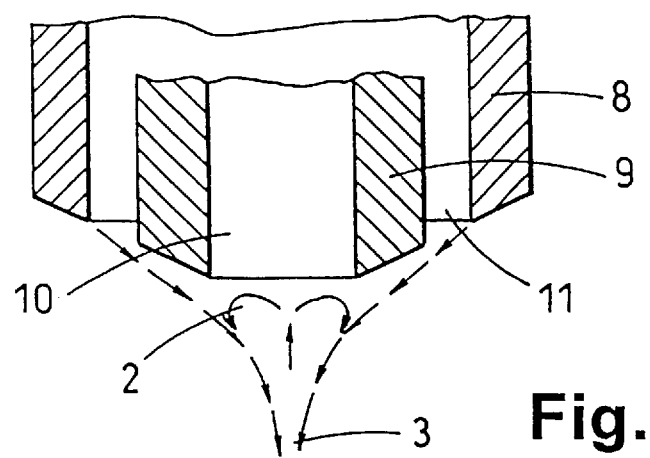

An alternative to the mixing arrangement of FIG. 5 is shown in cross section in FIG. 6, in which two coaxial cylinders (8) and (9) form two flowchannels (10) and (11). This arrangement has advantages and may induce a greater degree of mixing in some cases, for example, when there is a significant disparity in the flow rates of liquids a and b.

(4) Discharging Device

For delivering droplets into the middle and lower respiratory system, it is important that droplets are fully, or partially electrically discharged.

Figure 7:
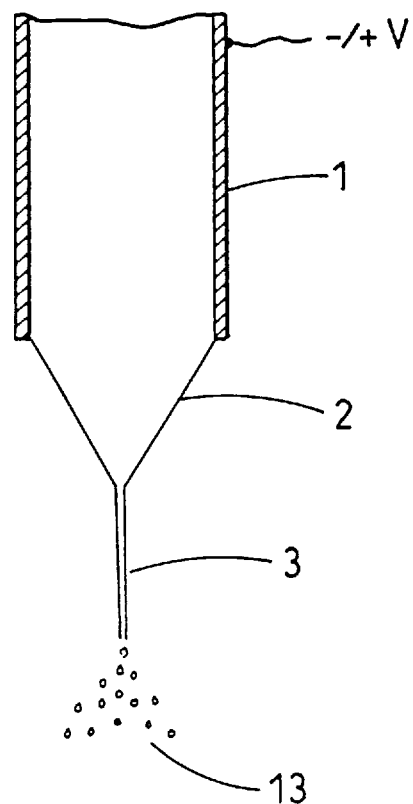
FIG. 7 shows part of a dispensing device embodying the invention.
Figure 7:
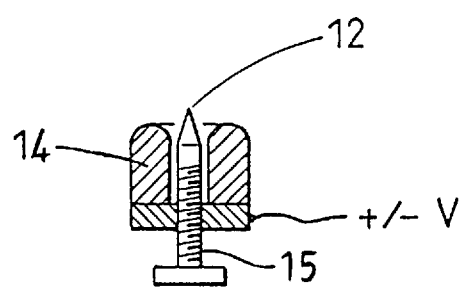

It has been found readily possible to discharge the droplets by one or both of two techniques, shown in FIG. 7. The first method, uses one or more earthed sharp-edged conductors or semiconductors (12) suitably located downstream of the jets, so that an opposite polarity charge is induced at the said edge. If the nozzle (or other electrode) potential and/or the space charge density of the spray cloud (13) is sufficient then the induced charge, and hence the field strength, at the edge will be sufficient to break down the surrounding gas, thus producing a large population of like-polarity gas ions which will be accelerated away from the edge, toward the cloud of charged droplets. The mobility of the gaseous ions is much greater than that of the charged droplets, and the droplets may thus become largely or totally neutralized by bombardment with opposite-polarity ions. Alternatively, an electrode of like polarity to the nozzle may be used to induce gas-ion generation at the sharp electrode.

The above described method, shown in cross section in FIG. 7 uses a passive electrode, which is the simplest method that we have found appropriate. However, it is dependent upon the nozzle or other like-polarity electrode or the droplet spray cloud having sufficient charge density to induce an air breakdown field (approximately 3 Mvolts/m). It may sometimes be preferred to connect the electrode (12) to earth through a source of d.c. high voltage, ensuring that the polarity is opposite to that of the spray cloud (13).

In each of the above devices, adjustment of the rate of ion bombardment may be provided by use of a field guard electrode (14) the controlling effect of which may be adjusted by screw (15) positioning, to increase or decrease the flow of gas ions to the spray and/or by the use of other electrodes of like polarity to the nozzle.

In these charge neutralization processes, opposite polarity gas ions bombard the charged droplets thus neutralizing them. In order to prevent these highly mobile gas ions from neutralizing the jets (3) or their respective cusps (2), before droplets, have been produced, it is preferable to direct the gas ions only, or predominantly, toward the comminuted matter.

I claim:

1. A dispensing device comprising an exposed, unshielded comminution site, means for supplying liquid to the comminution site, means for charging the comminution site to a potential for causing electrohydrodynamic comminution of liquid supplied to the comminution site, a discharge electrode for at least partially discharging comminuted matter, means for charging the discharge electrode to a polarity opposite to that of the comminution site to cause ionization of gaseous molecules in the vicinity of the discharge electrode, the discharge electrode being arranged so as to face towards the comminution site to cause gaseous ions produced by the discharge electrode to be directed towards the comminution site to at least partially discharge comminuted matter produced by the comminution site.

2. A device according to claim 1, further comprising a field guard electrode located so as to regulate the discharge of comminuted matter by the discharge electrode.

3. A device according to claim 2, wherein the field guard electrode is arranged to effect such regulation by adjustably altering the effective shape of the discharge electrode by adjustably enclosing or surrounding the discharge electrode.

4. A device according to claim 2, wherein the field guard electrode is an annular electrode surrounding the discharge electrode.

5. A device according to claim 3, wherein the field guard electrode is an annular electrode surrounding the discharge electrode.

6. A device according to claim 1, wherein the discharge electrode is surrounded by an annular field electrode which screw threadly engages a section of the discharge electrode so as to be movable towards and away from a top of the discharge electrode facing the comminution site for controlling the degree of discharge effected by the discharge electrode.

7. A device according to claim 11, wherein the comminution site comprises means for mixing two liquids prior to comminution.

8. A device according to claim 2, wherein the comminution site comprises means for mixing two liquids prior to comminution.

9. A device according to claim 3, wherein the comminution site comprises means for mixing two liquids prior to comminution.

10. A device according to claim 4, wherein the comminution site comprises means for mixing two liquids prior to comminution.

11. A device according to claim 5, wherein the comminution site comprises means for mixing two liquids prior to comminution.

12. A device according to claim 11 adapted to dispense a biocide, insecticide, perfume or aroma.

13. A device according to claim 11, wherein the liquid supplying means comprises first and second electrodes spaced apart along a liquid supply conduit with one of the electrodes being arranged to be coupled to a high voltage for generating an electric field to cause ions to stream from the high voltage electrode thereby inducing liquid flow by viscous drag.

14. An inhaler comprising a device in accordance with claim 1.

15. A device according to claim 11 adapted to dispense a biocide, insecticide, perfume or aroma.

* * * * *

UNITED STATES PATENT AND TRADEMARK OFFICE
CERTIFICATE OF CORRECTION

PATENT NO. : 5,813,614
DATED : September 29, 1998
INVENTOR(S) : Ronald Alan Coffee It is certified that error appears in the above-identified patent and that said Letters Patent is hereby corrected as shown below:

Claims 7, 12, 13 and 15, line 1 change "11" to --1--.

Signed and Sealed this

Sixth Day of July, 1999

Attest:

Attesting Officer

Q. TODD DICKINSON

Acting Commissioner of Patents and Trademarks